United States Patent [19]

Daniel

[11] 4,355,176
[45] Oct. 19, 1982

[54] OXYDEHYDROGENATION PROCESS FOR PREPARING METHACRYLIC ACID AND ITS LOWER ALKYL ESTERS

[75] Inventor: Chelliah Daniel, Columbus, Ohio

[73] Assignee: Ashland Oil, Inc., Ashland, Ky.

[21] Appl. No.: 319,353

[22] Filed: Nov. 9, 1981

[51] Int. Cl.³ .................... C07C 51/377; C07C 57/05; C07C 67/317; C07C 69/54
[52] U.S. Cl. .................................... 562/599; 252/435; 252/437; 560/214
[58] Field of Search .................. 562/599; 560/214; 252/435, 437; 260/405.5

[56] References Cited

U.S. PATENT DOCUMENTS 3,948,959  4/1976  Cavaterra et al. ............... 562/599
4,298,755  11/1981  Daniel et al. ..................... 562/599

Primary Examiner—Vivian Garner
Attorney, Agent, or Firm—John F. Jones

[57] ABSTRACT

Isobutyric acid or a lower alkyl ester thereof is oxidatively dehydrogenated in the vapor phase producing the corresponding $\alpha,\beta$-olefinically unsaturated derivative by contact with a heterogeneous catalyst in the presence of molecular oxygen. The catalyst is composed of the calcined phosphates of iron, silver and niobium.

4 Claims, No Drawings

OXYDEHYDROGENATION PROCESS FOR PREPARING METHACRYLIC ACID AND ITS LOWER ALKYL ESTERS

BACKGROUND OF THE INVENTION

1. Field of the Invention

This invention relates to the conversion of isobutyric acid or its equivalents and lower alkyl esters thereof correspondingly to methacrylic acid or its equivalents and lower alkyl esters thereof.

2. Description of the Prior Art

There exists considerable prior art relating to the oxydehydrogenation of the lower saturated aliphatic monocarboxylic acids to produce the corresponding $\alpha,\beta$-olefinically unsaturated acids. Early work in this area involved thermal, vapor phase oxydehydrogenation of the saturated aliphatic carboxylic acid in the presence of oxygen and iodine. This approach has not been particularly successful from a commercial standpoint. This is understandably so inasmuch as iodine is costly, exhibits extreme corrosivity properties and poses considerable problems in realizing complete recovery of the comparatively large amounts thereof required in the process. The heterogeneous catalytic method for oxydehydrogenation according to the prior art appears to be the more attractive route to the commercial production of $\alpha,\beta$-olefinically unsaturated monocarboxylic acids. The prior art heterogeneous oxydehydrogenation catalysts useful for this purpose include some heteropoly acids, such as phosphomolybdic acid, optionally with tungsten and/or vanadium. Another type of catalyst included in the prior art is iron phosphate.

Iron phosphate subjected to calcination exists in several crystalline phases or species. It is not known at this time which species is or are catalytically active. There is evidence that the presence of certain extrinsic metal components in the catalyst preparation serve to facilitate the formation of the active catalyst. For instance, U.S. Pat. No. 3,948,959 discloses that an alkali or alkaline earth metal can be the extrinsic metal for this purpose.

SUMMARY OF THE INVENTION

In accordance with this invention, a catalytic process is provided for the oxidative dehydrogenation of a saturated aliphatic monocarboxylic acid or lower alkyl ester thereof, such as isobutyric acid or methyl isobutyrate, to the corresponding $\alpha,\beta$-olefinically unsaturated derivative, such as methacrylic acid or methyl methacrylate. The process of this invention comprises contacting a heterogeneous catalyst at a temperature in the range of from 300°–500° C. with a mixture of the saturated aliphatic monocarboxylic acid and molecular oxygen, said catalyst being a calcined silver, niobium, iron phosphate. The catalyst useful in the process of this invention can be further defined by the gram-atom empirical formula $Fe_aAg_bNb_cP_dO_x$ wherein a is 0.05–1.0, b is 0.005–1.0, c is 0.001–1.0, d is 0.05–3.0 and x represents the number of oxygens required to satisfy the uncombined positive valences of the other elements shown in the formula.

DESCRIPTION OF THE PREFERRED EMBODIMENT

There are a number of techniques which can be used for preparing the catalyst useful in the process of this invention. Of these, the more facile methods involve preparing the integral catalyst composition prior to calcination. This can be done by the so-called slurry method or the precipitation method. In the latter method an aqueous solution of salts of the metals and phosphoric acid is first prepared and is then neutralized with an appropriate base so as to precipitate the mixed metal phosphates. The precipitate is washed and dried prior to calcination. In the alternative, one can add ammonium phosphate to a solution of the metal salts causing direct precipitation of the metal phosphates.

As indicated, any water-soluble salt of iron and silver can be used in the preparation of the solution. The nitrate salts are suitable water-soluble salts for this purpose and are preferred because of their ready availability and desirable solubility characteristics.

The so-called slurry method is the preferred catalyst preparation method because of its convenience. In accordance with this procedure the aqueous solution of the iron, silver and niobium salts together with the phosphoric acid is obtained as previously noted. The solution is then heated with stirring to remove water and this is continued until the mass is so thick it cannot be stirred. The resulting residue is then broken up and heated to a moderately elevated temperature in the order of about 120° C. until the mass is completely dried. The resulting solid is sized and calcined. Suitable calcination temperatures range from 400°–550° C. Applicable periods of calcination range from 2–30 hours although longer periods can be used if desired.

The use of a support or carrier for the catalyst is included in this invention. The support can be included in either of the catalyst preparation methods mentioned above. For instance, in the slurry method colloidal silica or any other form of silica as well as other support material such as alumina, pumice, zirconia, quartz, titanium dioxide, carbon, silicon, carbide, etc., can be included prior to the water removal step. Similarly, the precipitation of the metal phosphates can be accomplished in the presence of suspended particles of the support material in the alternate method described above.

The process of this invention can be carried out using the catalyst in the form of a fluidized bed reactor, a stirred tank reactor or in a fixed bed or packed bed reactor or any combination of these types of reactor configurations. Because of the convenience associated with the use of a fixed bed reactor in a small scale operation, such a reactor will be exemplified herein. In the preferred mode of operation the feed to the reactor comprises a preheated gaseous mixture of the saturated aliphatic monocarboxylic acid, molecular oxygen, steam and inert diluent gas. A preheat temperature in the range of about 300° to 350° C. is customarily used. The oxydehydrogenation reaction can be carried out in the range of from 300° to 500° C. More generally a temperature of from 375° to 425° C. provides for optimum processing.

The mole ratio of molecular oxygen to carboxylic acid is from 0.5 to 1.5 and more preferably from 0.7 to 0.75 in the case where the carboxylic acid is isobutyric acid per se. Although steam is not necessary for the reaction, its presence is desirable in the feed because it is believed to act beneficially as a heat sink and in minimizing combustion of the carboxylic acid to undesirable waste products. The mole ratio of water to the carboxylic acid in the feed should be from about 8 to 20. The optimum ratio is from 12 to 15.

Another important parameter is the concentration of the organic reactant in the feed. The reactant carboxylic acid or ester should be present in the feed in from 0.1 to 20 mole percent.

From the standpoint of achieving a reasonable throughput combined with an acceptable yield, the concentration of the reactant in the feed is from about 3-6 mole percent, concentration of reactant in the feed is controlled to a large degree by the amount of inert gas present. The preferred inert gas or diluent is nitrogen although other inert gases such as carbon dioxide, helium, argon, and the like are suitable. Air is a very convenient source of oxygen plus inert diluent.

Another important parameter is contact time in the process of this invention. Contact or reaction time is defined for the purpose of this invention as the catalyst volume divided by the volume of gas feed per second at the reaction temperature. The catalyst volume is the bulk volume occupied by the catalyst in the reactor. The term catalyst in this sense not only includes the iron, silver, niobium phosphate itself but also includes the support if present. Accordingly, reaction times can range from 0.1 to 1.0 second. The reaction is preferably carried out at or near atmospheric pressure although the use of higher pressures up to about 10 atmospheres is contemplated.

The process of this invention is further illustrated in the following specific examples.

EXAMPLE I

This example illustrates the use of the slurry method for preparing the catalyst on a silica carrier. A slurry containing 500 cc. water, 202.4 grams of iron nitrate, 17 grams of silver nitrate, 18.25 grams of niobium oxalate, 57.2 grams of 85.0% phosphoric acid, and 200.0 grams of silica in the form of a 40% wt. solids aqueous silica sol was heated and stirred on a hot plate until it became so thick it could no longer be stirred. The resulting solid was calcined at 450° C. for 16 hours. The final catalyst had the gram-atom empirical formula $Fe_{1.0}Ag_{0.2}Nb_{0.1}P_{1.0}O_4/SiO_2 45\%$.

EXAMPLE II

This example illustrates the use of the catalyst described in Example I in the oxydehydrogenation of isobutyric acid to produce methacrylic acid. The procedure consisted of feeding a preheated mixture of isobutyric acid, oxygen, nitrogen and steam through a stainless steel tube of ½" O.D. (⅜" I.D.) and approximately 18" in length containing the catalyst as a 15 cc packed bed maintained at the reaction temperature.

The preheater consisted of a length of stainless steel tubing similar to the reactor but packed with glass beads. Any carbon dioxide formed in the course of the reaction was absorbed in an Ascarite tube protected by a calcium sulfate absorber for any uncondensed water. The condensed organic product was separated from the water, collected and analyzed by the internal standard method of gas chromatography.

Selectivity to methacrylic acid represents the mole ratio of methacrylic acid found in the reaction effluent to that of the isobutyric acid consumed in the reaction.

The feed to the reactor consisted of isobutyric acid:oxygen:water:nitrogen in the corresponding mole ratio of 5.4:3.9:64.8:25.9. The reaction temperature was 400° C. and the contact time was 0.55 second. In a series of such experiments in which the ratio of isobutyric acid:water (cc./hr.) was varied the conversions and selectivities shown in the following table were obtained.

TABLE I

| Isobutyric Acid/H₂O cc/hr | % Conversion of Isobutyric Acid | % Selectivity to Methacrylic Acid |
|---|---|---|
| 5.5/13.3 | 69.5 | 84.5 |
| 8.8/20 | 63.1 | 78.3 |
| 8.8/20 | 74.7 | 80.3 |
| 8.8/26.4 | 72.7 | 82.8 |
| 8.8/20 | 77.5 | 77.8 |
| 8.8/20 | 78.9 | 80.2 |
| 8.8/20 | 79.5 | 80.0 |

EXAMPLE III

In a manner similar to that described in Example I a catalyst was prepared from a slurry of 404.4 g. of ferric nitrate, 25.0 g. of silver nitrate, 5.0 g. of niobium oxalate, 114.4 g. of 85% phosphoric acid and 13.1 g. of silica (in the form of a 40% solids aqueous silica sol) and 500 ml. of deionized water. The slurry was dried with stirring and dried at 120° C. for 15 hours. The resulting solid was calcined at 450° C. for 16 hours. The final catalyst had the gram-atom empirical formula $Fe_{1.0}Ag_{0.15}Nb_{0.01}P_{1.1}O_4/SiO_2 3.5\%$.

EXAMPLE IV

The catalyst mentioned in Example III was used to convert isobutyric acid to methacrylic acid by the procedure of Example II. The feed to the reactor was isobutyric acid:oxygen:water:nitrogen in the corresponding mole ratio of 5.4:3.9:64.8:25.9. The reaction temperature was 400° C. and the contact time was 0.55 second. In a series of such experiments the ratio of isobutyric acid:water (cc./hr.) was varied, the conversions and selectivities shown in Table II were obtained.

TABLE II

| Isobutyric Acid/H₂O cc/hr | % Conversion of Isobutyric Acid | % Selectivity to Methacrylic Acid |
|---|---|---|
| 8.4/13.3 | 68.6 | 72.0 |
| 8.4/20.1 | 80.1 | 74.5 |
| 8.4/20.5 | 79.5 | 73.9 |
| 8.4/25.0 | 80.4 | 76.4 |
| 8.4/10.0 | 40.0 | 85.3 |
| 8.4/15.0 | 76.5 | 70.7 |
| 8.4/8.4 | 66.3 | 76.3 |
| 3.4/15 | 74.3 | 74.4 |

I claim:

1. In a process for the catalytic conversion of isobutyric acid or a lower alkyl ester thereof to the corresponding $\alpha,\beta$-olefinically unsaturated derivative by oxydehydrogenation wherein a catalyst is contacted with a gaseous stream containing said acid or ester and molecular oxygen at a temperature between about 300° and 500° C.: the improvement comprising using as catalyst a material having the gram-atom empirical formula $Fe_aAg_bNb_cP_dO_x$ wherein a is 0.05–1.0, b is 0.005–1.0, c is 0.001–1.0, d is 0.05–3.0, and x is determined by satisfying the sum of the unshared positive valences of the other elements shown in the formula.

2. The process of claim 1 wherein isobutyric acid is converted to methacrylic acid.

3. The process of claim 2 wherein the catalyst has the gram-atom empirical formula $Fe_{1.0}Ag_{0.2}Nb_{0.1}P_{1.0}O_4$.

4. The process of claim 2 wherein the catalyst has the gram-atom empirical formula $Fe_{1.0}Ag_{0.15}Nb_{0.01}P_{1.1}O_4$.

* * * * *